United States Patent [19]
Keil et al.

[11] Patent Number: 5,690,924
[45] Date of Patent: Nov. 25, 1997

[54] HAIR TREATMENT COMPOSITIONS

[75] Inventors: Wolfgang Keil, Mülheim; Bernd Stein, Hösbach; Jürgen Schmenger, Weiterstadt, all of Germany

[73] Assignee: Wella AG, Darmstadt, Germany

[21] Appl. No.: 667,580

[22] Filed: Jul. 12, 1996

[30] Foreign Application Priority Data

Aug. 24, 1995 [DE] Germany ............ 195 31 145.0

[51] Int. Cl.⁶ ...................................... A61K 31/74
[52] U.S. Cl. ........................................ 429/78.03
[58] Field of Search ............................ 424/78.03

[56] References Cited

FOREIGN PATENT DOCUMENTS

| | | |
|---|---|---|
| 0492657A1 | 12/1991 | European Pat. Off. . |
| 0524612 | 7/1992 | European Pat. Off. . |
| 0636357 | 3/1994 | European Pat. Off. . |
| 93 10967 | 9/1993 | France . |
| 4234743 | 10/1992 | Germany . |
| 4343378 | 12/1993 | Germany . |
| WO87/07618 | 6/1986 | WIPO . |

OTHER PUBLICATIONS

Chemical Abstracts 123: 17449, 1993, Dupuis.

*Primary Examiner*—Zohreh Fay
*Attorney, Agent, or Firm*—Michael J. Striker

[57] ABSTRACT

The hair treatment composition is based on a polymer combination including (A) 0.01 to 40 percent by weight of a salt formed from a chitosan having a molecular weight of at least 100.000 g/mol and 2-pyrrolidon-5-carboxylic acid, and (B) 0.01 to 50 percent by weight of at least one synthetic, film-forming anionic or nonionic hair fixing polymer, or natural film-forming hair fixing polymer. This hair treatment composition provides an improved action in regard to combability, care sensitivity, load on the hair, brushability, hair feel, hair fixing action and residues left on the hair.

5 Claims, No Drawings

HAIR TREATMENT COMPOSITIONS

BACKGROUND OF THE INVENTION

The present invention concerns a composition for treating hair based on a polymer combination of (A) 0.01 to 40 percent by weight of a salt, which is formed from a chitosan with a molecular weight of at least 100,000 g/mol and from 2-pyrrolidon-5-carboxylic acid and (B) 0.01 to 50 percent by weight of at least one synthetic, film-forming, nonionic or anionic hair fixing polymer or a natural, film-forming hair fixing polymer.

Hair treatment compositions, which give the hair a certain shape or form, are known in different application forms. An imperfect combination of hair care properties and strong fixing properties for hair is often a disadvantage of the known hair treatment compositions. Hair fixing agents usually comprise solutions of film-forming, natural or synthetic polymers. Furthermore it is known that cationic polymers provide hair care action which is based on the hair affinity of these polymers. The cationic polymers used up to now have the disadvantage that they are absorbed not only on the hair but also on cotton fabric and mucous membranes. Especially for hair fixing compositions in the form of fixing foams this can lead to a stain formation on pieces of cloths, towels and similar cotton fabrics. Furthermore the cationic polymers used up to now in hair fixing composition contribute considerably to formulation or dispensing costs.

A hair fixing composition is described in German Published Patent Application DE-OS 42 34 743 which contains (1) at least one water-soluble, halogen-free organic solvent and (2) a compound selected from a group described in the reference which is water-insoluble at room temperature, but water soluble in the composition besides natural or synthetic, film-forming polymers. chitosan, among others, is used in combination with pyrrolidone carboxylic acid as a suitable film-forming polymer. A non-film-forming and non-fixing polysiloxane-polyether copolymer is used, among others, as the water-insoluble compound. A hair treatment composition is not disclosed there with two film-forming polymers. This hair treatment composition provides a satisfactory fixing of hair and, at the same time, improves combability, feel and appearance of the hair treated with it. Although this composition can provide satisfactory hair fixing together with hair care properties, there is a further need for an improved hair treatment composition providing a better combination of strong fixing properties and outstanding hair care.

SUMMARY OF THE INVENTION

It is an object of the present invention to provide a hair treatment composition, which has hair care properties as well as fixing properties, advantageously free of cationic polymers used up to now for hair care and does not have the above-described disadvantages.

It has now been found that a composition for treating hair based on a polymer combination with a content of (A) a salt, which comprises a chitosan with a molecular weight of at least 100,000 g/mol and 2-pyrrolidon-5-carboxylic acid and, (B) at least one synthetic, film-forming, nonionic or anionic hair fixing polymer or a natural, film-forming, hair fixing polymer, fulfills the objectives of the invention in an outstanding manner.

The composition according to the invention provides improved combability, care sensitivity, load on the hair, brushability, feel, hair fixing and residue remaining on the hair.

Furthermore it was surprisingly and unexpectedly discovered that an addition of at least one silicon polymer to the composition produces an improvement in care properties, which does not occur on addition of a silicon polymer for film-forming without the simultaneous presence of the high molecular weight chitosonium-pyrrolidone carboxylate of component (A).

The hair treatment composition according to the invention contains 0.01 to 40 percent by weight, advantageously 0.05 to 10 percent by weight, of a salt, which comprises a high molecular weight, water-soluble chitosan neutralized with 2-pyrrolidon-5-carboxylic acid. The base chitosan has a molecular weight of over 100,000 g/mol, advantageously from 200,000 to 700,000 g/mol, and a deacetylization degree of from 10 to 99%, advantageously from 60 to 99%. A suitable chitosan is, for example, obtained from the firm KYOWA OIL & FAT, Japan, under the trademark Flonac®. It has a molecular weight of from 300,000 to 700,000 g/mol and is deacetylated from 75 to 90%. This chitosan is neutralized with 2-pyrrolidon-5-carboxylic acid. A suitable chitosonium pyrrolidone-carboxylate is, for example, marketed under the trademark KYTAMER® PC of the firm Amercol, Edison, N.J., USA. The chitosan contained there has a molecular weight of 200,000 to 300,000 g/mol and is deacetylated at 70 to 85%.

The composition according to the invention contains, as component (B), 0.01 to 50 percent by weight, advantageously 0.5 to 20 percent by weight, of at least one synthetic, film-forming, nonionic or anionic hair fixing polymer or a natural, film-forming, hair fixing polymer in addition to the salt of the modified natural film-forming and hair fixing polymers of component (A). The hair fixing polymers can be used individually or in a mixture.

Suitable synthetic nonionic, film-forming, hair fixing polymers are, e.g., homopolymers of vinyl pyrrolidone, which, e.g., are marketed under the trademark LUVISKOL® K of BASF, Ludwigshafen, Germany or PVP-K of ISP, Wayne, N.J., USA and homopolymers of N-vinyl formamide, which, e.g., are marketed under the tradename PVF of National Starch, USA. Additional suitable synthetic film-forming, nonionic hair fixing polymers are, e.g., copolymerizates of vinyl pyrrolidone and vinyl acetate, which, e.g., are marketed under the trademark LUVISKOL® VA of the firm BASF, Ludwigshafen, Germany; terepolymers of vinyl pyrrolidone, vinyl acetate and vinyl propionate, which, e.g., are marketed under the trademark LUVISKOL® VAP of BASF, Ludwigshafen, Germany; polyacrylamides, which, e.g., are marketed under the trademark AKYPOMINE® P 191 of CHEM-Y, Emmerich, Germany, or SEPIGEL® 305 of SEPPIC, USA; polyvinyl alcohols, which, e.g., are marketed by Du Pont or VINOL® 523/540 of Air Products, USA and polyethylene glycols having a molecular weight of 800 to 20,000 g/mol, which, for example, are marketed under the trademark LIPOXOL® 1000 of HÜLS AG, Germany, PLURACOL E 4000 of BASF, Germany or UPIWAX® 20000 of UPI.

Suitable film-forming, anionic polymers include, e.g., crotonic acid-vinyl acetate copolymers, which are marketed, e.g., in the form of a 60% solution in isopropanol/water under the trademark ARISTOFLEX® of Hoechst, Germany.

Suitable natural film-forming polymers with hair fixing action include low molecular weight chitosan with a molecular weight of 30,000 to 70,000 g/mol, which for example is marketed by KYOWA OIL & FAT, Japan. Different saccharide types are used, e.g. polysaccharides or mixtures of oligo-, mono- and disaccharides, which for example are marketed under the trademark C-PUR® of Cerestar, Brüssel, Belgium. Additional suitable natural polymers are Chinese balsamic resin and cellulose derivatives, e.g. hydroxypropyl cellulose with a molecular weight of 30,000 to 50,000 g/mol, which, e.g., is marketed under the trademark NISSO SL® of Lehmann & Voss, Hamburg, Germany.

The weight ratio of component (A) to component (B) is advantageously from 1:5000 to 10:1. The weight ratio range of (A) to (B) from 1:100 to 1:1 is particularly preferred.

The "film-forming, hair fixing polymers" are those polymers which, when used alone in 0.1 to 5% by weight aqueous, alcoholic or aqueous-alcoholic solution, deposit a polymer film on the hair and the hair is fixed in this manner.

In a preferred embodiment of the invention the composition for treating hair also includes from 0.01 to 10 percent by weight, advantageously 0.05 to 2 percent by weight, of at least one silicon polymer, as a third component (C) in addition to component (A) and component (B).

Suitable silicon polymers are, for example, polydimethyl siloxane (CFTA: dimethicone), α-hydroxy-ω-hydroxypolyoxydimethylsilylene (CFTA: dimethiconol), cyclic dimethylpolysiloxane (CFTA: cyclomethicone), trimethyl(octadecyloxy)silane (CFTA: stearoxytrimethylsilane), dimethylsiloxane-glycol copolymer (CFTA: dimethicone copolyol), dimethylsiloxane-aminoalkylsiloxane copolymer with hydroxy end groups (CFTA: amodimethicone), monomethylpolysiloxane with lauryl side chains and polyoxyethylene end chains and/or polyoxypropylene end chains, (CFTA: lauryl methicone copolyol), dimethyl siloxane-glycol copolymer-acetate (CFTA: dimethicone copolyol acetate), dimethylsiloxane-aminoalkylsiloxane copolymer with trimethylsilyl end groups (CFTA: trimethylsilylamodimethicone). Preferred silicone polymers are: dimethicones, which, e.g., are marketed by Wacker, München, Germany under the tradename SILOXANE F-221 or by Dow Corning, Europe, Brussels, Belgium under the tradename Dow Corning Fluid 200/0.65 cs; cyclomethicones, which, e.g., are marketed under the tradename DOW CORNING 244 Fluid of Dow Corning, Europe/ Belgium or ABIL® K4 of Goldschmidt, Germany; dimethiconols, which, e.g., are marketed under the tradename SILICONE FLUID F-212 of Wacker, Germany, or UNISIL® SF-R of UPI.

The names shown in parentheses are the names for the cosmetic materials of the CFTA (Cosmetic, Toilet and Fragrance Association, USA).

Mixtures of silicone polymers are suitable as, e.g., a mixture of dimethicone and dimethiconol, which, for example, is marketed by Dow Corning, Europe/Belgium, under the tradename DOW CORNING 1403 Fluid.

Additional suitable silicon polymers are dimethicone copolyols, which are marketed under the trademark SURFACTANT 193 of Dow Corning, Europe/Belgium or SILWET® L of Union Carbide, U.S.A.; amodimethicones, which for example are marketed under the trademark SANDOPERM® FE of Sandoz, Switzerland or SM 2059 of General Electric, U.S.A.; lauryl methicone copolyol, which is marketed under the tradename DOW CORNING Q2-5200 of Dow Corning, Europe/Belgium; trimethylsilylamodimethicones, which are marketed under the tradename Dow Corning Q2-8220 of Dow Corning, Europe/Belgium, or SILICONE FLUID F-801 of Wacker, Germany; dimethicone copolyol acetate, which are marketed under the tradename SILICONE FLUID VP or BELSIL® DMC 6033 of Wacker, Germany and trimethyl (octadecyloxy)silane (CFTA: stearoxytrimethylsilane), which, e.g., is marketed by Dow Corning Europe/Belgium, under the tradename DOW CORNING 580 wax.

The composition according to the invention is preferably prepared in aqueous or in aqueous-alcoholic media, however it is also possible to provide it as a water-free preparation.

As alcohols, the composition according to the invention can contain lower alcohols with 1 to 4 carbon atoms usually used for cosmetic applications, such as ethanol and isopropanol.

Understandably the composition according to the invention can also contain standard cosmetic additives, for example non-fixing, non-ionic polymers, such as polyethylene glyols with a molecular weight of 600 g/mol, non-fixing anionic polymers and non-fixing natural polymers as well as their combinations in an amount of advantageously 0.01 to 50 percent by weight; perfume oils in an amount of advantageously 0.01 to 5 percent by weight; turbidity inducing agents, such as ethylene glycol distearate, in an amount of advantageously 0.01 to 5% by weight, wetting agents or emulsifiers from the classes of anionic, cationic, amphoteric or nonionogenic surface-active substances such as fatty alcohol sulfates, ethoxylated fatty alcohols, fatty acid alkanol amides such as the ester of hydrogenated castor oil fatty acids in an amount of advantageously 0.1 to 30% by weight; humectants, dyes, light protecting agents, antioxidants, shine imparting substances and preservatives in an amount of advantageously 0.01 to 10% by weight.

The composition according to the invention can be used in different applications, e.g. in aerosol preparations such as foams or sprays. It can also be used as a non-aerosol preparation, which is dispensed by a pump or as "pump and spray". The composition can be an O/W and W/O emulsion but can also be in the form of a gel, wax or microemulsion.

The composition according to the invention can also be a hair dyeing agent or hair care treatment agent such as a hair dye composition, a hair rinse composition and a shampoo.

If the composition according to the invention is in the form of an aerosol hair spray or an aerosol hair lacquer, it additionally contains 15 to 85 percent by weight, preferably 25 to 75 percent by weight, of a propellant and is filled in a pressurized container.

Lower alkanes, for example n-butane, i-butane and propane, or their mixtures with dimethylether, are suitable as the above-mentioned propellant. Also pressurized gaseous propellants, such as $N_2$, $N_2O$ and $CO_2$ and their mixtures, are suitable as the propellant.

The composition according to the invention for fixing hair can also be a non-aerosol hair spray or a non-aerosol hair laquer sprayed with the help of a mechanically operated spraying apparatus or device.

The term "mechanical spraying devices or apparatuses" means those devices which allow a liquid to be sprayed without the use of a propellant. A spray pump or an elastic container provided with a spray valve, in which the cosmetic composition according to the invention is filled under pressure, is suitable for use as a mechanical spraying device. The cosmetic composition can be continuously dispensed from the elastic container in which it is filled by contraction of the elastic container with the spray valve open.

"Hair treatment" means the treatment of human hair on the head primarily for the purpose of setting the hair in a hair-do, for hair care or for cleaning of the hair.

The making of a concentrate having a reduced water content is possible with the polymer combination according to the invention. After transport and, if necessary, after storage, the concentrate is converted into the ready-to-use hair treatment composition by addition of the required amount of water.

The cooperation of the high molecular weight chitosonium-pyrrolidone carboxylate (A) and the hair fixing polymers (B) produces a hair care preparation, which is distinguished by a compact hair care film formed on the hair. An improvement in combability, care sensitivity, load on the hair, brushability, feel, and hair fixing results. Furthermore a reduction in the amount of residue on the hair and a reduction of formulation costs also results.

An additional definite increase in the above-mentioned hair care effects is obtained when silicon polymers are added to the combination of the high molecular weight chitosonium pyrrolidone carboxylate (A) and the hair fixing polymer (B).

The following examples should explain the invention in greater detail without limitation of the claims appended hereinbelow.

EXAMPLES

Example 1

Foam Fixing Composition Having a Strong Fixing Effect

| | |
|---|---|
| 0.25 g | chitosan, deacetylated 75 to 90%, molecular weight = 300,000 to 700,009 g/mol, (Flonac ® of KYOWA OIL & FAT, Japan) |
| 0.20 g | 2-pyrrolidon-5-carboxylic acid |
| 2.00 g | polyvinyl pyrrolidone |
| 0.50 g | chitosan, molecular weight = 30,000 to 70,000 g/mol |
| 0.15 g | formic acid, 85% by weight |
| 0.10 g | cetyltrimethylammonium chloride |
| 0.10 g | isopropanol |
| 96.70 g | water |
| 100.00 g | |

Example 2

Liquid Fixing Agent with Strong Fixing Effect

| | |
|---|---|
| 0.20 g | chitosonium pyrrolidone carboxylate, 70 to 80% deacetylated, molecular weight = 200,000 to 300,000 g/mol (KYTAMER ® PC of Amerchol, USA) |
| 1.00 g | vinyl acetate-crotonic acid copolymer, 60% solution in isopropanol/water (ARISTOFLEX ® of Hoechst, Germany) |
| 2.58 g | glycerol |
| 50.00 g | ethanol |
| 46.22 g | water |
| 100.00 g | |

Example 3

Gel-form Fixing Composition Having a Strong Fixing Effect

| | |
|---|---|
| 0.15 g | chitosan, deacetylated 75 to 90%, molecular weight = 300,000 to 700,000 g/mol, (Flonac ® of KYOWA OIL & FAT, Japan) |
| 0.10 g | 2-pyrrolidon-5-carboxylic acid |
| 3.00 g | vinyl pyrrolidone-vinyl acetate copolymer |
| 1.00 g | hydroxyethylcellulose |
| 5.00 g | glycerol |
| 90.75 g | water |
| 100.00 g | |

Example 4

Foam Fixing Composition for Stressed Hair

| | |
|---|---|
| 0.15 g | chitosan, deacetylated 75 to 90%, molecular weight = 300,000 to 700,000 g/mol, (Flonac ® of KYOWA OIL & FAT, Japan) |
| 0.10 g | 2-pyrrolidon-5-carboxylic acid |
| 2.00 g | polyvinylpyrrolidone |
| 0.30 g | 13% a-hydro-m-hydroxy-polyoxydimethylsilylene in cyclodimethylpolysiloxane (DOW Corning Q2 1401 of Dow Corning Europe/Belgium) |
| 5.00 g | 1,2-propylene glycol |
| 0.10 g | cetyltrimethylammonium chloride |
| 0.10 g | isopropanol |
| 92.25 g | water |
| 100.00 g | |

Example 5

Foam Fixing Composition for Extra Strong Hold

| | |
|---|---|
| 0.15 g | chitosan, deacetylated 75 to 90%, molecular weight = 300,000 to 700,000 g/mol, (Flonac ® of KYOWA OIL & FAT, Japan) |
| 0.10 g | 2-pyrrolidon-5-carboxylic acid |
| 2.00 g | polyvinylpyrrolidone |
| 2.00 g | glucose syrup, 64% oligosaccharides, (C-PUR ® 01924 of Cerestar, Belgium) |
| 0.30 g | polyoxyethylen(4)lauryl ether |
| 0.10 g | cetyltrimethylammonium chloride |
| 0.10 g | isopropanol |
| 40.00 g | ethanol |
| 55.25 g | water |
| 100.00 g | |

Example 6

Gel-form Fixing Agent with Natural Polymers

| | |
|---|---|
| 0.15 g | chitosonium pyrrolidone carboxylate, 70 to 85% deacetylated, molecular weight = 200,000 to 300,000 g/mol (KYTAMER ® PC of Amercol, USA) |
| 5.00 g | glucose syrup, 64% oligosaccharides, (C-PUR ® 01924 of Cerestar, Belgium) |
| 5.00 g | sorbitol syrup |
| 2.00 g | ergot resin (Sclerotium Gum) |
| 87.85 g | water |
| 100.00 g | |

Example 7

Sprayed Fixing Composition for Fixing Hair

| | |
|---|---|
| 0.10 g | chitosan, deacetylated 75 to 90%, molecular weight = 300,000 to 700,000 g/mol, (Flonac ® of KYOWA OIL & FAT, Japan) |
| 0.05 g | 2-pyrrolidon-5-carboxylic acid |
| 0.75 g | vinyl pyrrolidone-vinyl acetate copolymer |
| 30.00 g | ethanol |
| 3.00 g | propylene glycol |
| 0.75 g | isopropanol |
| 65.35 g | water |
| 100.00 g | |

Example 8

Hair Wax

| | |
|---|---|
| 0.30 g | chitosonium pyrrolidone carboxylate, 70 to 85% deacetylated, molecular weight = 200,000 to 300,000 g/mol (KYTAMER® PC of Amercol, USA) |
| 30.00 g | polyethylene glylcol, molecular weight = 3,000 g/mol |
| 44.70 g | polyethylene glycol, molecular weight = 600 g/mol |
| 15.00 g | glycerol |
| 10.00 g | hydrogenated castor oil, ethoxylated with 45 mol ethylene oxide |
| 100.00 g | |

Example 9

Non-aerosol Hair Spray

| | |
|---|---|
| 0.15 g | chitosan, deacetylated 75 to 90%, molecular weight = 300,000 to 700,000 g/mol, (Flonac® of KYOWA OIL & FAT, Japan) |
| 0.10 g | 2-pyrrolidon-5-carboxylic acid |
| 3.00 g | vinyl pyrrolidone-vinyl acetate copolymer |
| 50.00 g | ethanol |
| 46.75 g | water |
| 100.00 g | |

Example 10

Hair Care Shampoo with Fixing Action

| | |
|---|---|
| 0.12 g | chitosonium pyrrolidone carboxylate, 70 to 85% deacetylated, molecular weight = 200,000 to 300,000 g/mol (KYTAMER® PC of Amercol, USA) |
| 1.00 g | vinylpyrrolidone-vinyl acetate copolymer |
| 30.00 g | sodium lauryl ether sulfate |
| 7.00 g | sodium chloride |
| 3.00 g | coconut oil fatty acid amidopropylbetaine |
| 0.40 g | hydrogenated castor oil, ethoxylated with 45 mol ethylene oxide |
| 0.20 g | perfume oil |
| 58.28 g | water |
| 100.00 g | |

Example 11

Dyeing and Fixing Composition

| | |
|---|---|
| 0.2500 g | chitosoniumpyrrolidone carboxylate, 70 to 85% deacetylated, molecular weight 200,000 to 300,000 g/mol (KYTAMER® PC of Amercol, USA) |
| 3.0000 g | vinylpyrrolidone-vinyl acetate copolymer |
| 50.0000 g | ethanol |
| 0.2000 g | perfume oil |
| 0.0700 g | 1-amino-4-(2',3'-dihydroxypropyl)amino-5-chloro-2-nitrobenzene |
| 0.0500 g | Basic Brown 17 (C.I. 12 251) |
| 0.0023 g | Basic Violet 14 (C.I. 42 510) |
| 0.0100 g | Basic Blue 7 (C.I. 42 595) |
| 46.4177 g | water |
| 100.0000 g | |

Example 12

Foam Fixing Concentrate

| | |
|---|---|
| 2.7 g | chitosan, deacetylated 75 to 90%, molecular weight = 300,000 to 700,000 g/mol, (Flonac® of KYOWA OIL & FAT, Japan) |
| 2.3 g | 2-pyrrolidon-5-carboxylic acid |
| 20.0 g | polyvinyl pyrrolidone |
| 10.00 g | dimethylsiloxane-glycol copolymer (Belsil® DMC 6031 of Wacker, Germany) |
| 65.0 g | water |
| 100.00 g | |

While the invention has been illustrated and described as embodied in hair treatment compositions, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A hair treatment composition based on a polymer combination, said hair treatment composition comprising
   (A) 0.01 to 40 percent by weight of a salt of a chitosan having a molecular weight of at least 100,000 g/mol and 2-pyrrolidon-5-carboxylic acid, and
   (B) 0.01 to 50 percent by weight of at least one member selected from the group consisting of synthetic, film-forming hair fixing nonionic polymers, synthetic anionic film-forming hair fixing polymers and natural, film-forming hair fixing polymers.

2. The hair treatment composition as defined in claim 1, wherein a weight ratio of said salt to said at least one member is in a range from 1:5,000 to 10:1.

3. The hair treatment composition as defined in claim 1, wherein said at least one hair fixing polymer is selected from the group consisting of polyvinyl pyrrolidone, vinyl pyrrolidone-vinyl acetate copolymers, vinyl pyrrolidone-vinyl acetate-vinyl propionate terpolymers, polyacrylamides, polyvinyl alcohols, polyethyene glycols having a molecular weight of 800 to 20,000 g/mol, crotonic acid-vinyl acetate copolymer, chitosan having a molecular weight of 30,000 to 70,000 g/mol, oligosaccharides, polysaccharides, Chinese balsamic resin and cellulose derivatives.

4. The hair treatment composition as defined in claim 1, further comprising from 0.01 to 10 percent by weight of at least one silicon polymer.

5. The hair treatment composition as defined in claim 4, wherein said at least one silicon polymer is selected from the group consisting of polydimethylsiloxane; dimethylsiloxane-glycol copolymer; cyclic dimethylpolysiloxane; α-hydroxy-ω-hydroxy-polyoxydimethylsilylene; dimethylsiloxane-aminoalkylsiloxane copolymer with hydroxy end groups; monomethylpolysiloxane having lauryl side chains and polyoxyethylene end chains; monomethylpolysiloxane having lauryl side chains and polyoxypropylene end chains; monomethylpolysiloxane having lauryl side chains, polyoxyethylene end chains and polyoxypropylene end chains; dimethylsiloxane-aminoalkylsiloxane copolymer with trimethylsilyl end groups; dimethylsiloxane-glycol copolymer acetate and trimethyl (octadecyloxy)silane.

* * * * *